(12) United States Patent
Huang et al.

(10) Patent No.: US 8,819,859 B1
(45) Date of Patent: Aug. 26, 2014

(54) APPARATUS OF ANALYZING A SAMPLE AND A METHOD FOR THE SAME

(71) Applicant: Taiwan Semiconductor Manufacturing Company, Ltd., Hsin-Chu (TW)

(72) Inventors: Yen-Kai Huang, Hsinchu (TW); Yuan-Chih Chu, New Taipei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/757,543

(22) Filed: Feb. 1, 2013

(51) Int. Cl.
   *G01N 13/16* (2006.01)
   *G01N 23/00* (2006.01)
   *G01B 5/28* (2006.01)

(52) U.S. Cl.
   USPC ...... 850/1; 850/5; 850/26; 250/306; 250/307; 250/310; 250/492.2; 250/492.3

(58) Field of Classification Search
   USPC .......... 850/1, 5, 26; 250/306.307, 310, 492.2, 250/492.3
   See application file for complete search history.

(56) References Cited

U.S. PATENT DOCUMENTS

| | | | | |
|---|---|---|---|---|
| 8,387,443 | B2 * | 3/2013 | King et al. | 73/105 |
| 2007/0194225 | A1 * | 8/2007 | Zorn | 250/306 |
| 2012/0206722 | A1 * | 8/2012 | Grigoropoulos et al. | 356/318 |
| 2013/0284894 | A1 * | 10/2013 | Freese et al. | 250/208.2 |

* cited by examiner

*Primary Examiner* — Nikita Wells
(74) *Attorney, Agent, or Firm* — Haynes and Boone, LLP

(57) ABSTRACT

The apparatus includes a probe tip configured to scan a substrate having a defect to attach the defect on the probe tip while scanning the substrate, a cantilever configured to integrate a holder holding at least one probe tip, a stage configured to secure the substrate, an electromagnetic radiation source configured to generate the electromagnetic radiation beam, and an electromagnetic radiation detector configured to receive the first electromagnetic radiation signal and the second electromagnetic radiation signal. A first electromagnetic radiation signal is generated while an electromagnetic radiation beam focuses on the probe tip. A second electromagnetic radiation signal is generated while the electromagnetic radiation beam focuses on the sample attached on the probe tip. A chemical analysis of the sample is executed by comparing a difference between the first electromagnetic radiation signal and the second electromagnetic radiation signal.

20 Claims, 4 Drawing Sheets

APPARATUS OF ANALYZING A SAMPLE AND A METHOD FOR THE SAME

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs.

Defect analysis is an important aspect of the IC industry. It is common for defects to occur in the substrate being fabricated, such as a wafer with one or more dies, as well as in masks used to fabricate the substrate. In light of the advanced scaling that has occurred, smaller defects become more critical, and more difficult to detect and analyze. Generally, tools such as a transmission electron microscope (TEM) or an energy-dispersing x-ray scanning electron microscope or energy dispersive X-ray spectroscopy (collectively referred to as EDX) are used for defect analysis. However, these tools often have difficulty with very small defects, and for handling background signals. Also, sample preparation for these tools are often very difficult to prepare, and sometime require destroying the item (e.g., wafer or mask) to be analyzed. Accordingly, what is needed is a method to analyze defects in a quicker and more accurate way.

BRIEF DESCRIPTION OF THE DRAWINGS

The present disclosure is best understood from the following detailed description when read with accompanying figures. It is emphasized that, in accordance with the standard practice in the industry, various features are not drawn to scale and are used for illustration purpose only. In fact, the dimension of the various features may be arbitrarily increased or reduced for clarity of discussion.

DETAILED DESCRIPTION

Figure 1:
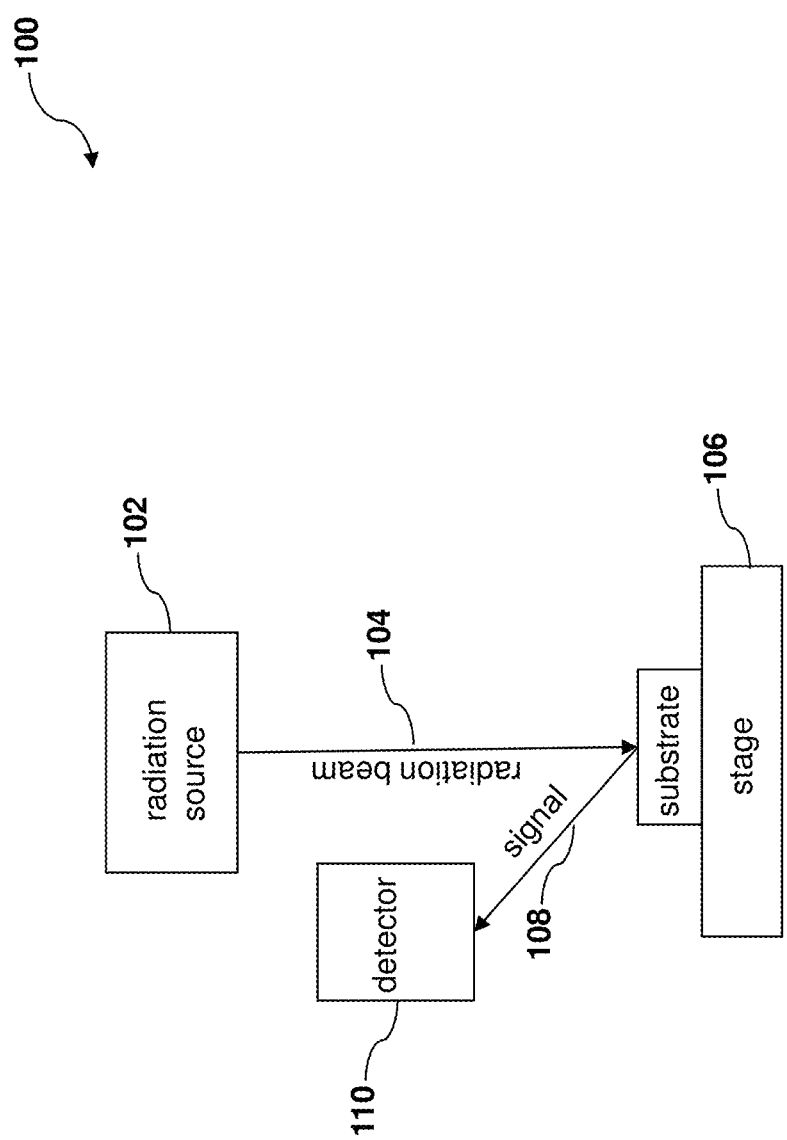
FIG. 1 is a diagram of an analytical tool according to one or more embodiments.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Referring now to FIG. 1, a diagram of an analytical tool 100 for analyzing a defect falling on a substrate is illustrated according to one or more embodiments. In the present embodiments, a defect is also referred to as a foreign defect or a particle. The analytical tool 100 includes an electromagnetic radiation source 102, an electromagnetic radiation beam 104, a stage 106, a signal 108, and a detector 110. It is understood that other configurations and inclusion or omission of various items in the analytical tool 100 may be possible. In the depicted embodiment, the analytical tool 100 is used to determine or characterize chemical component(s) of a defect, such as a particle from an IC device, and find the source of the defect in a semiconductor fab. A substrate may include a wafer substrate, a mask substrate, a semiconductor device, or a piece of material from a wafer substrate, a mask substrate or a semiconductor device.

The electromagnetic radiation source 102 includes a source generating the electromagnetic radiation beam 104, such as a light beam, an electron beam, or an ion beam. The stage 106 is a place securing a substrate and providing movement in X, Y and X direction or rotation for a substrate. The stage 106 includes motors, roller guides, and tables; secures a sample; provides the accurate position and movement of a substrate in X, Y and Z directions; and allow a electromagnetic radiation beam focusing on a defect falling on a substrate. The signal 108 includes an electromagnetic radiation pulse signal generated by an interaction between a defect falling on a substrate and the electromagnetic radiation beam 104 focused on the defect. The detector 110 receives the signal 108 from a defect falling on a substrate and converts the signal 108 to a chemical characterization, such as a spectrum of a chemical function group or a chemical component profile of a defect falling on a substrate using a computer. The detector 110 includes a light detector, an electron detector, or an ion detector. The detector 110 also includes a processor to convert an electromagnetic radiation pulse signal to a voltage signal used by a computer.

As shown in FIG. 1A, when the electromagnetic radiation beam 104 emitted from the electromagnetic radiation source 102 is focused on a defect residing in/on a substrate secured on the stage 106, the signal 108 is detected by the detect 110. Depending on the electromagnetic radiation source 102 and the detector 110, a chemical characterization of the defect, such as a chemical function spectrum or a chemical component profile of the defect is determined using the electromagnetic radiation beam 104. For example, a chemical function group of a defect is determined by Fourier transfer infrared spectroscopy (FTIR). In another example, a chemical component profile of a defect is determined by EDX. In one embodiment, by knowing the chemical component profile of a defect on a substrate using EDX, a contamination source generating the defect can be identified and addressed.

Continuing with the present embodiment, while performing an EDX technique on a defect on a substrate, a signal detected by a detector not only includes a signal from the defect but also from the substrate itself. In the present embodiments, a signal from a substrate is referred as to a background signal or a noise. Sometimes, a signal of a defect on a substrate is the same as the background signal and therefor an EDX spectrum of the defect cannot identify chemical components of the defect.

Figure 2A:
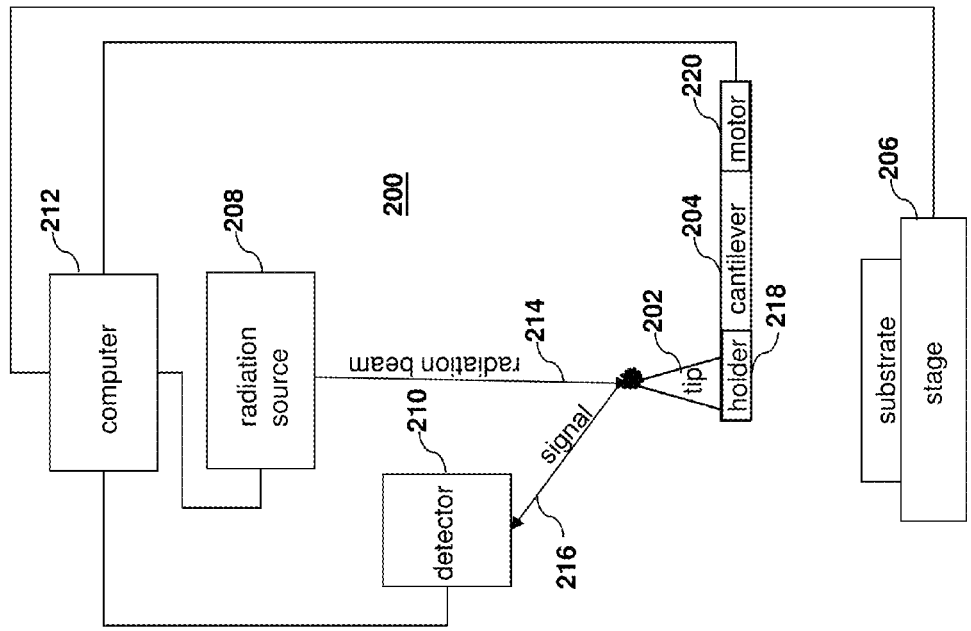
FIGS. 2A and 2B are diagrams of an apparatus for charactering a defect on a substrate for benefiting from one or more embodiments.
Figure 2B:
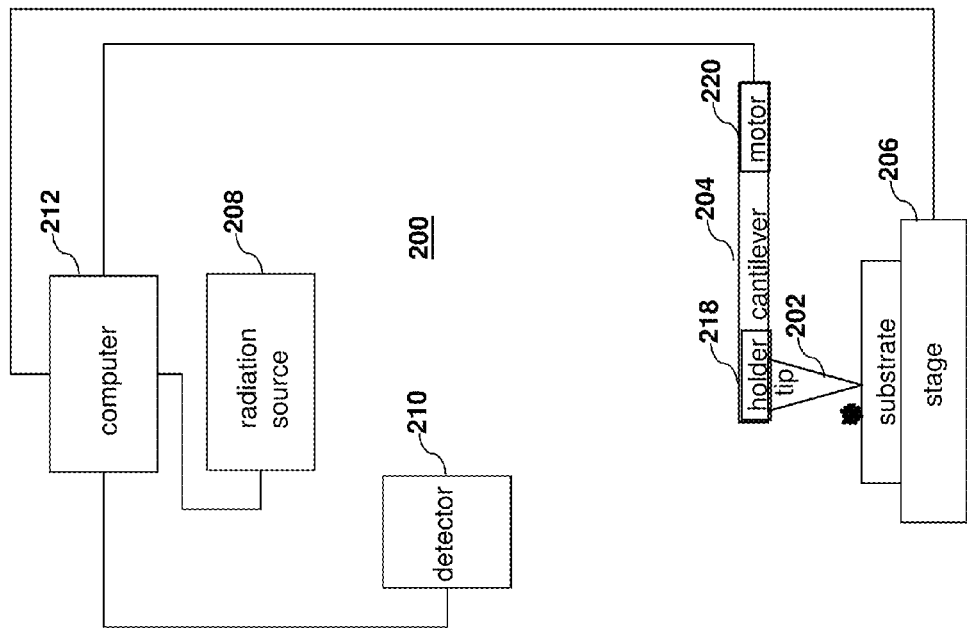
Figure 3A:
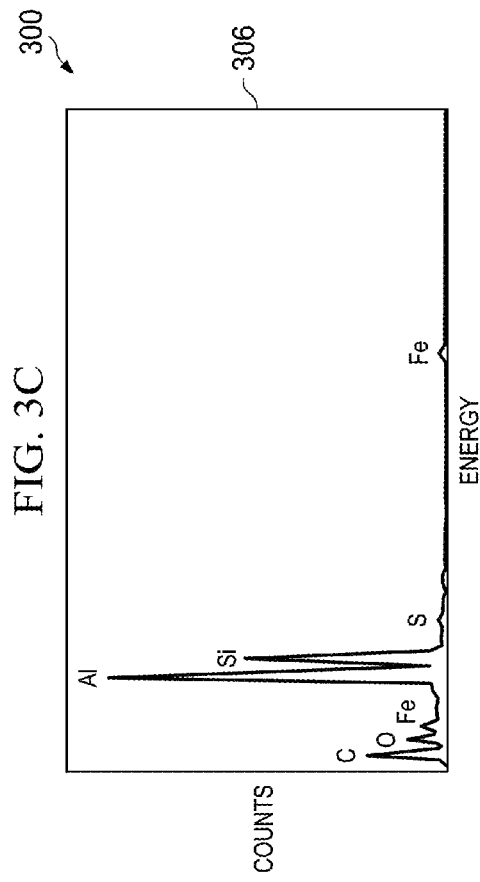
FIGS. 3A-D are examples of characterizing a defect on a substrate for benefiting from one or more embodiments.
Figure 3C:
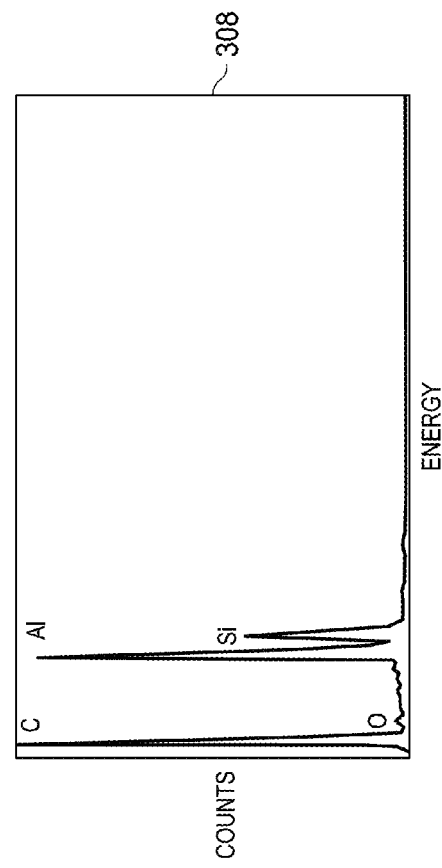
Figure 3B:
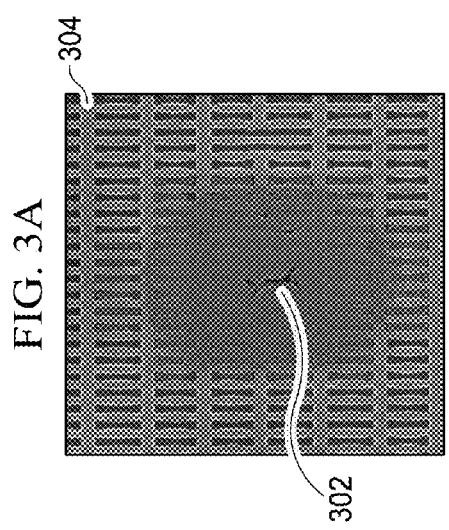
Figure 3D:
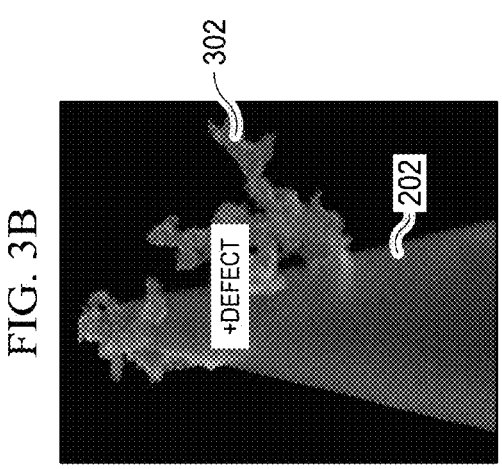

Referring to FIGS. 2A and 2B, diagrams of an apparatus 200 for analyzing a sample embedded in a substrate are illustrated for implementing one or more embodiments. In the present embodiments, a sample is also referred to as a defect. A sample includes an inorganic compound, an organic compound, or combination thereof. The apparatus 200 has a function of detaching a defect embedded in a substrate from the substrate using a probe tip as shown in FIG. 2A and analyzing the sample attached on the probe tip using an electromagnetic radiation beam as shown in FIG. 2B. The apparatus 200 includes a probe tip 202, a cantilever 204, a stage 206, an electromagnetic radiation source 208, a detector 210, and a computer 212. The cantilever 204 includes a holder 218 and a motor 220. It is understood that other configurations and inclusion or omission of various items in the apparatus 200 may be possible. The apparatus 200 is an example of embodiments, and is not intended to limit the present invention beyond what is explicitly recited in the claims.

The probe tip 202 is configured to install on the holder 218 integrated into the cantilever 204. The probe tip 202 includes a metal, a metal compound, a carbon-based material, or another material. The probe tip 202 has an adhesive property so that the probe tip 202 can pick up a sample embedded in a substrate and attaches the sample on the probe tip 202 while scanning surface of a substrate, such as a wafer or a photomask. In some embodiments, the probe tip 202 scans a designated area on a substrate in a scanning rate, picks up and attaches a sample embedded in the substrate to the probe tip 202, moves away from the surface of the substrate with the sample attached on the probe tip 202, and allows the electromagnetic radiation beam 214 focused on the sample attached to the probe tip 202 for analysis. For example, the probe tip 202 can attach a particle from a wafer when scanning a wafer, move away from the wafer, and allow an electron beam to focus on the particle to analyze chemical component of the particle. Further, by knowing the chemical component of the particle, it is possible to locate a source of the defect.

The cantilever 204 is configured to support the probe tip 202 and connect to the computer 206. The cantilever 204 integrates the holder 218, holding one or more probe tips 202. The cantilever 204 also integrates the motor 220, moving and rotating the probe tip 202 away from a surface of a substrate. The cantilever 204 may include a metal or a metal alloy. The cantilever 204 is designed to the support probe tip 202, move in X, Y or Z direction, or rotate with the probe tip 202 during and after scanning. For example, the cantilever 204 supports the probe tip 202 while the probe tip 202 is scanning a substrate, and then moves or rotates the probe tip 202 in the designated angle with a sample attached to the probe tip 202 after scanning, so that the electromagnetic radiation beam 214 can focus on the sample and a chemical analysis can be performed on the sample without interference from the substrate.

The stage 206 is for securing a substrate and providing relative movement of the substrate when the probe tip 202 is scanning. The stage 206 connects to the computer 212. The stage 206 includes motors, roller guides, and tables; secures a substrate by vacuum; and provides the accurate position and movement of the substrate in X, Y and Z directions during the probe tip 202 scanning. In one embodiment, scanning a substrate includes moving the stage 206 while the probe tip 202 is in a static position. In another embodiment, scanning a substrate includes moving the probe tip 202 by moving the cantilever 204 while the stage 206 is in a static position.

The electromagnetic radiation source 208 is configured to provide the electromagnetic radiation beam 214 for performing a chemical analysis or a chemical characterization on a sample picked from a substrate by the probe tip 202. The electromagnetic radiation source 208 connects to the computer 212. The electromagnetic radiation source 208 includes a source generating the electromagnetic radiation beam 214, such as a light beam, an electron beam, or an ion beam. In the present embodiments, various electromagnetic radiation beams are used for chemical analysis. For examples, an electron beam is used to determine chemical component of the sample in the apparatus 200, such as in an EDX or in an Auger electron spectroscopy (AES); a light beam is used to determine a chemical functional group of the sample in the apparatus 200, such as in an FTIR; and an ion beam is used to determine chemical components of the sample in the apparatus 200, such as in a secondary ion mass spectroscopy (SIMS).

The electromagnetic radiation detector 210 is configured to detect the electromagnetic radiation signal 216 emitted from a sample attached on the probe tip 202 when the electromagnetic radiation beam 214 is projected or focused on the sample. In the present embodiments, an electromagnetic radiation signal is also referred to as a signal. The electromagnetic radiation detector 208 connects to the computer 210. The electromagnetic radiation detector 208 includes a converter converting an electromagnetic radiation signal to a voltage signal for the computer 212 processing. The electromagnetic radiation detector 210 includes a light detector, an electron detector, or an ion detector. In the present embodiments, various detectors are used for chemical characterization of a sample attached on the probe tip 202. For example, an electron detector is used to determine chemical components of the defect in the apparatus 200, such as in an EDX or an AES, a light detector is used to determine a chemical functional group of the sample in the apparatus 200, such as in a FTIR; and an ion detector is used determine chemical component of the defect in the apparatus 200, such as in a SIMS.

The computer 212 is a standard, general-purpose computer, including a processor, a database (memory), and interface. The computer 212 may be a single computer or a distributed computer, and connects to various components such as the cantilever 204, the stage 206, the electromagnetic radiation source 208, and the electromagnetic radiation detector 210 as shown in FIGS. 2A and 2B. The computer 212 includes one or more software programs for controlling one or more components of the apparatus 200 during and after scanning, picking a sample from the substrate, analyzing the sample, and summarizing a chemical characterization of the sample.

The computer 212 controls the stage movement in X, Y and Z direction during the probe tip 212 scanning to pick up a sample in an interested area. The computer 212 also controls the cantilever 204 to move or rotate so that the sample attached at the probe tip 212 is moved away from the substrate. The computer 212 also controls an electromagnetic radiation beam emitted from the electromagnetic radiation source 208 to focus on the sample for a chemical characterization of the defect. The computer 212 further controls the detector 210 to receive a signal and convert the signal to a signal for processing. The computer 212 also provides a report of the chemical characterization of the sample.

The electromagnetic radiation beam 214 is generated by the electromagnetic radiation source 208 and is focused on a defect attached on the probe tip 202. The electromagnetic radiation beam 214 includes a light beam, an electron beam or an ion beam. The electromagnetic radiation signal 216 is generated by an interaction between the electromagnetic radiation beam 214 and the sample attached on the probe tip 202. The electromagnetic radiation signal 216 includes a light radiation pulse, an electron radiation pulse, or an ion radiation pulse. The electromagnetic radiation signal 216 may reveal chemical characterizations of the sample attached on the probe tip 202, such as chemical structure, chemical function group, or chemical component of the sample.

For example, while a light beam is focus on a sample (a defect), the light beam interacts with a chemical bond of the sample and a signal generated by the interaction uncovers a chemical function group of the sample. This principle is used in optical spectroscopy, such as FTIR. In another example, while an electron beam is focused on a sample (e.g. a defect), the electron beam interacts with orbit electrons of a chemical element of the sample and a signal generated by the interaction reveals chemical component of the sample. This principle is used in an electron spectroscopy, such as an EDX or AES. In an alternative example, while an electron beam is focused on a sample (e.g. a defect), the ion beam interacts with orbit electrons of a chemical element of the sample and a signal generated by the interaction uncovers chemical component of the sample. This principle is used in another electron spectroscopy, such as SIMS.

According to one or more embodiments, the apparatus 200 can perform a chemical characterization on a sample, such as a defect attached on the probe tip 202, with minimum or without interference from the environment surrounding the sample. For example, a substrate, such as a wafer, with a defect embedded on the substrate is provided to the apparatus 200 for chemical characterization of the defect to locate a possible source of the defect. The probe tip 202 scans an interested area on the substrate loaded on the stage 206 and attaches the defect on the probe tip 202; the defect moves away from the substrate by moving or rotating the probe tip 202 attached on the cantilever 204; the electromagnetic radiation source 208, such as an electron source, generates the electromagnetic radiation beam 214, such as an electron beam, to focus on the defect; the electromagnetic radiation detector 210 receive a signal, such as an escaped electron, generated between an interaction between the electron beam and orbit electron of a chemical element in the defect, and converts the signal to a voltage signal; and the computer 212 receives the voltage signal and generates a report of chemical component of the defect. In some embodiments, because the probe tip 202 is significantly different from a defect attached on the tip and an interference of the probe tip 202 is minimized, performing a chemical characterization on a defect is more accurate and quick.

Referring to the examples of FIGS. 3A-D, a defect 302 is embedded on a wafer or mask 304, the foreign defect 302 is attached on the probe tip 202 using the apparatus 200 as shown in FIGS. 2A and 2B, a chemical component profile 306 is generated using the electromagnetic radiation source 208 and the electromagnetic radiation detector 210, and the defect 302 includes elements Fe and S calculated by the computer 212 by comparing the chemical component profile 306 with a chemical component profile 308 of the probe tip 202. Further, a possible contamination or defect source is located by knowing the chemical component of the defect. That is, certain tools or processing steps are known to be associated with the defect 302, and once the chemical properties of the defect are identified and analyzed, the corresponding tool or processing step can be identified.

Figure 4:
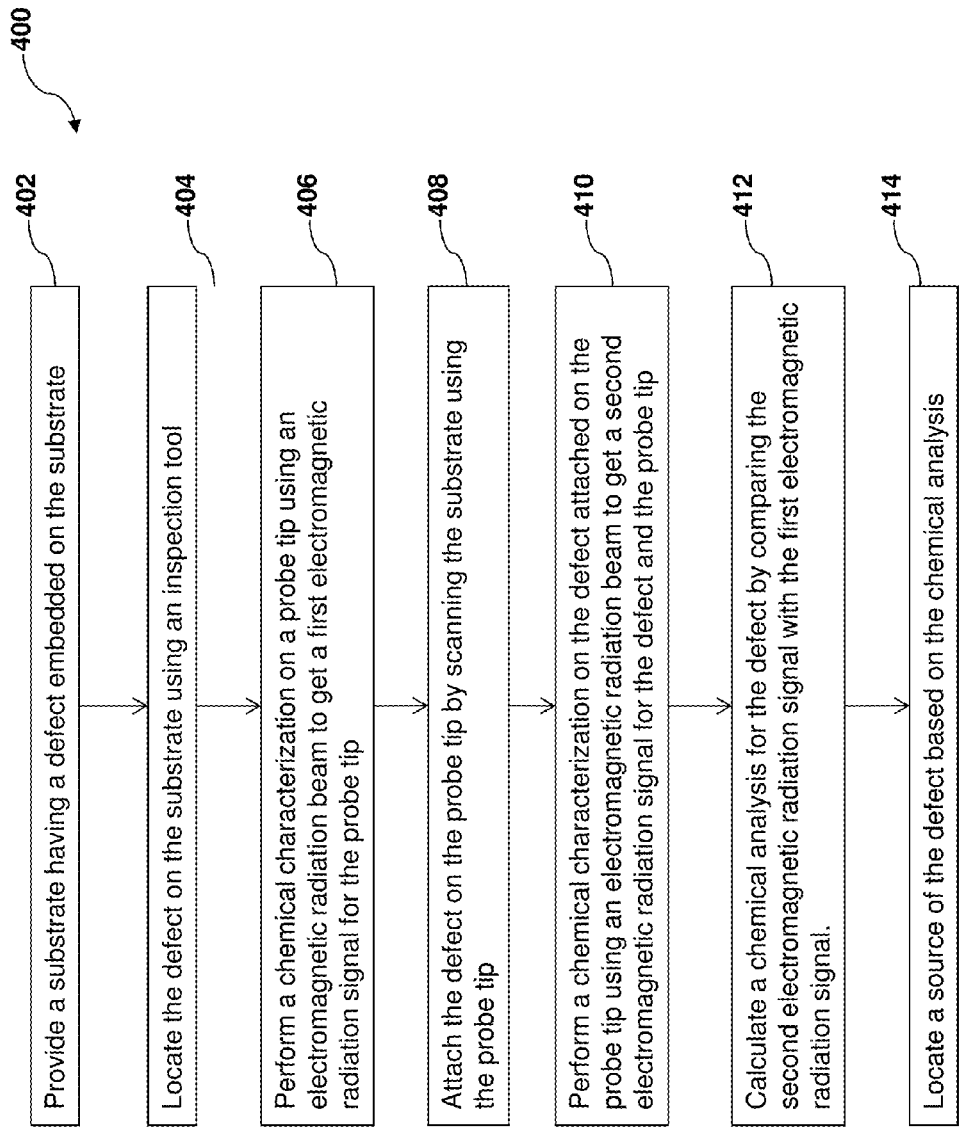
FIG. 4 is a flow char of characterizing a defect on a substrate for benefiting from one or more embodiments.

Referring to FIG. 4, a flow chart of a method 400 for characterizing a sample embedded on a substrate using the apparatus 200 is illustrated for benefiting from one or more embodiments. The method 400 begins at step 402 by providing a substrate having a sample embedded therein. In the present embodiments, the substrate is a wafer, such as a silicon wafer. Alternatively or additionally, the substrate includes another elementary semiconductor, such as germanium; a compound semiconductor including silicon carbide, gallium arsenic, gallium phosphide, indium phosphide, indium arsenide, and/or indium antimonide; or an alloy semiconductor including SiGe, GaAsP, AlInAs, AlGaAs, GaInAs, GaInP, and/or GaInAsP. In yet another alternative, the substrate includes a semiconductor on insulator (SOI) structure. The substrate further includes various doped features, such as n-type wells and/or p-type wells, formed by ion implantation or diffusion. The substrate also includes various isolation features, such as shallow trench isolation (STI), formed by a process, such as a process including etching to form various trenches and then depositing to fill the trench with a dielectric material.

In the present embodiments, the substrate also includes one or more conductive and/or dielectric films. In the present embodiment, the dielectric film may include silicon oxide, high k dielectric material film, or a combination of silicon oxide and high k dielectric material, and the conductive thin film for the gate electrode film may include doped polysilicon, or a metal, such as aluminum (Al), copper (Cu), tungsten (W), nickel (Ni), titanium (Ti), gold (Au), platinum (Pt) or alloy of the metals thereof.

In the present embodiments, a sample, such as a defect, has previously formed on the substrate during some part of the wafer fabrication. For example, the defect is formed while depositing a conducting or a non-conductive film on the wafer. In another example, the defect is formed while baking the wafer in an oven or on a hot plate chamber. In another example, the defect is formed while measuring the wafer with a measurement tool.

The method 400 proceeds to step 404 to locate the sample embedded in the substrate. In the present example, an interested area on the wafer is identified, such as a die area or a wafer edge. The probe tip is moved to the interested area to scan and pick up a sample. Step 404 includes inspecting the substrate using an inspection tool, such as a wafer inspection tool or a photomask inspection tool. Step 404 also includes sending coordinates of the sample to a computer. The probe tip can then be positioned for the next step.

The method 400 proceeds to step 406 by performing a chemical characterization on the probe tip using an electromagnetic radiation beam. Step 406 provides a first electromagnetic radiation signal generated from an interaction between the electromagnetic radiation beam and the probe tip. Step 406 includes focusing an electromagnetic radiation beam on the probe tip and collecting an electromagnetic radiation signal generated from an interaction between a probe tip and an electromagnetic radiation beam focused on the probe tip using a detector. The first electromagnetic radiation signal is then stored in a database of a computer system, as a baseline for the probe tip. Step 410 also includes generating a chemical analysis for the probe tip using the first electromagnetic radiation signal by the computer. In the present embodiments, this step is also referred to as a calibration of a probe tip using an electromagnetic radiation beam.

The method 400 proceeds to step 408 by attaching the sample embedded in/on the substrate onto the probe tip. Step 408 includes scanning the interested area and picking up the sample by the probe tip during or after scanning. In some embodiments, scanning an interested area on the substrate includes running the probe tip near a top surface of the substrate. In other embodiments, scanning an interested area on a substrate includes using the probe tip in a morphology tool, such as a probe tip in an atomic force microscope (AFM). The probe tip with sample can then be positioned for the next step.

The method 400 proceeds to step 410 by performing a chemical characterization on the sample attached on a probe tip. This includes focusing an electromagnetic radiation beam on the sample and collecting a second electromagnetic radiation signal generated therefrom. Step 410 further includes converting the electromagnetic signal to a voltage signal for a computer to process.

The method 400 proceeds to step 412 by calculating a chemical analysis for the sample. Step 412 includes comparing the second electromagnetic radiation signal with the first electromagnetic radiation signal. Step 412 may include subtracting the first electromagnetic radiation signal from the second electromagnetic radiation signal. In the present embodiments, a chemical analysis includes a chemical function group, a chemical component profile, or a chemical component report.

In some embodiments, performing a chemical characterization of the sample includes unloading the probe tip with the sample attached to the probe tip, loading the sample attached on the probe tip to an analytical tool, and performing the chemical characterization on the sample. In one example, a chemical function group is determined by loading the probe tip with the sample to a FTIR and using a light beam of the FTIR focusing on the sample attached on the probe tip. In another example, a chemical component profile is generated by loading the probe tip with the sample to an EDX and using an electron beam of the EDX focusing on the sample.

In other embodiments, performing a chemical characterization of a sample includes using the apparatus 200 as shown in FIGS. 2A and 2B by rotating the cantilever 204 such that the sample attached to the probe tip 202 moves away from the substrate and an electromagnetic radiation beam focuses on the sample for a chemical characterization. In one example, the electromagnetic radiation beam includes a light beam and a chemical function group of the sample is determined by the light beam interaction with the sample. In another example, the electromagnetic radiation beam includes an electron beam and a chemical component profile of the sample is determined by the electron beam interaction with the sample.

The method 400 proceeds to step 414 by locating a source of the defect. This includes tracing a possible source of the defect based on the chemical analysis, such as a chemical component profile or a chemical function group of the defect. Examples include a resist splash on a wafer, a chemical buildup on a deposition chamber or a heating chamber, a haze growth on a photomask, and a chemical scratch on a wafer. Step 414 also includes performing a maintenance procedure to clean, replace or fix the source of the defect.

In the present embodiments, it is understood that additional steps can be provided before, during, and after the method 400, and some the steps described can be replaced, eliminated, or moved around for additional embodiments of the method 400. The method 400 is example embodiments, and is not intended to limit the present invention beyond what is explicitly recited in the claims.

Thus, the present disclosure describes an apparatus for analyzing a sample embedded in a substrate. The apparatus includes a probe tip configured to scan a substrate having a sample to attach the sample on the probe tip while scanning the substrate, wherein a first electromagnetic radiation signal is generated while an electromagnetic radiation beam focusing on the probe tip and a second electromagnetic radiation signal is generated when the electromagnetic radiation beam focusing on the sample attached on the probe tip, a cantilever configured to integrate a holder holding at least one probe tip, wherein the cantilever moves the sample attached on the probe tip away from the substrate so that the electromagnetic radiation beam can focus on the sample attached on the probe tip, a stage configured to secure the substrate, an electromagnetic radiation source configured to generate the electromagnetic radiation beam, and an electromagnetic radiation detector configured to receive the first electromagnetic radiation signal and the second electromagnetic radiation signal. The apparatus also includes a computer configured to connect the cantilever, the stage, the electromagnetic radiation source, and the electromagnetic radiation detector.

In one or more embodiments, a method of analyzing a sample embedded in a substrate is described. The method includes receiving a substrate having a sample embedded in the substrate, performing a first chemical characterization on a probe tip using an electromagnetic radiation beam to generate a first electromagnetic radiation signal by the probe tip, scanning the substrate using the probe tip, wherein the probe tip picks the sample from the substrate while scanning the substrate, performing a second chemical characterization on the sample attached on the probe tip using the electromagnetic radiation beam to generate a second electromagnetic radiation signal by the sample and the probe tip, and generating a chemical analysis for the sample by comparing the second electromagnetic radiation signal with the first electromagnetic radiation signal. The method also includes inspecting the substrate using an inspection tool to locate the sample on the substrate. The method further includes locating a source generating the sample by using the chemical analysis for the sample.

In some embodiments, a method of analyzing a defect embedded in a substrate is presented. The method includes receiving a substrate having a defect embedded in the substrate, performing a first chemical characterization on a probe tip using an electromagnetic radiation beam to generate a first electromagnetic radiation signal by the probe tip, scanning the substrate using the probe tip installed on a holder integrated to a cantilever, wherein the probe tip picks the defect from the substrate while scanning the substrate, moving the defect attached on the probe tip away from substrate so that the electromagnetic radiation beam focuses on the defect attached on the probe tip to generate a second electromagnetic radiation signal by the defect and the probe tip without interference from the substrate, and generating a chemical analysis for the defect by using a difference between the first electromagnetic radiation signal and the second electromagnetic radiation signal. The method further includes locating a contamination source generating the defect by using the chemical analysis for the defect so that the contamination source is fixed.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:
1. An apparatus comprising:
a stage for securing a substrate;
a probe tip configured to be positioned in a first location near the substrate, by which the probe tip can secure a sample from the substrate, and in a second location, different from the first location, by which the secured sample can be exposed to a radiation source;

the radiation source configured to generate and direct the electromagnetic radiation beam onto the secured sample; and an electromagnetic radiation detector configured to receive the electromagnetic radiation beam after engaging with the sample.

2. The apparatus of claim 1, further comprising a computer configured to move the probe tip between the first and second locations.

3. The apparatus of claim 1, further comprising:
a cantilever includes a motor for rotating the probe tip between the first and second locations.

4. The apparatus of claim 1, wherein the probe tip includes a metal, a metal compound or a carbon-based material.

5. The apparatus of claim 1, wherein the radiation source includes a light source, an ion source, or an electron source.

6. The apparatus of claim 5, wherein the electromagnetic radiation beam includes a light beam, an ion beam, or an electron beam.

7. The apparatus of claim 6, wherein the electromagnetic radiation detector includes a light detector, an electron detector, or an ion detector.

8. The apparatus of claim 2, wherein the computer is configured to move the stage relative to the probe tip.

9. A method comprising:
receiving a substrate having a sample embedded therein;
performing a first chemical characterization on a probe tip using an electromagnetic radiation beam to generate a first electromagnetic radiation signal for the probe tip;
scanning the substrate using the probe tip, wherein the probe tip secures to the sample while scanning the substrate;
performing a second chemical characterization on the sample secured to the probe tip using the electromagnetic radiation beam to generate a second electromagnetic radiation signal; and
generating a chemical analysis for the sample by comparing the second electromagnetic radiation signal with the first electromagnetic radiation signal.

10. The method of claim 9, further comprising inspecting the substrate using an inspection tool to locate the sample on the substrate.

11. The method of claim 9, further comprising locating a source generating the sample by using the chemical analysis for the sample.

12. The method of claim 9, wherein using an electromagnetic radiation beam includes using a light beam, an ion beam, or an electron beam.

13. The method of claim 9, wherein the first electromagnetic radiation signal is different from the second electromagnetic radiation signal.

14. The method of claim 9, wherein comparing the second electromagnetic radiation signal with the first electromagnetic radiation signal includes using a difference between the first electromagnetic radiation signal and the second electromagnetic radiation signal.

15. The method of claim 9, wherein generating the chemical analysis includes identifying a chemical component, or a chemical functional group of the sample.

16. A method comprising:
receiving a substrate having a defect;
performing a first chemical characterization on a probe tip using an electromagnetic radiation beam to generate a first electromagnetic radiation signal;
scanning the substrate using the probe tip installed on a holder integrated to a cantilever, wherein the probe tip attaches to the defect from the substrate while scanning;
moving the defect attached on the probe tip away from substrate
after moving performing a second chemical characterization on the probe tip and the attached defect using another electromagnetic radiation beam to generate a second electromagnetic radiation signal; and
generating a chemical analysis for the defect by comparing a difference between the first electromagnetic radiation signal and the second electromagnetic radiation signal.

17. The method of claim 16, further comprising locating a candidate contamination source by using the chemical analysis.

18. The method of claim 16, wherein moving the defect attached on the probe tip includes rotating the cantilever.

19. The method of claim 16, wherein moving the defect attached on the probe tip includes removing the probe tip from the holder.

20. The method of claim 16, wherein generating the chemical analysis for the defect includes identifying a chemical function group of the defect.

* * * * *